United States Patent [19]

Rupp et al.

[11] Patent Number: 5,153,189
[45] Date of Patent: Oct. 6, 1992

[54] SULFIMIDOPEROXYCARBOXYLIC ACIDS

[75] Inventors: Walter Rupp, Königstein/Taunus; Hanspeter Gethöffer, Frankfurt am Main; Gerd Reinhardt; Frank Jaekel, both of Kelkheim, all of Fed. Rep. of Germany

[73] Assignee: Hoechst Aktiengesellschaft, Frankfurt am Main, Fed. Rep. of Germany

[21] Appl. No.: 793,803

[22] Filed: Nov. 18, 1991

[30] Foreign Application Priority Data

Nov. 16, 1990 [DE] Fed. Rep. of Germany ....... 4036647

[51] Int. Cl.$^5$ .................... A01N 43/80; A01N 43/72; C07D 275/06; C07D 275/02
[52] U.S. Cl. ................................ 514/211; 514/222.5; 514/372; 514/373; 540/488; 544/3; 548/210; 548/213; 252/186.42
[58] Field of Search .................... 548/210, 213; 544/3; 540/488; 514/211, 222.5, 372, 373

[56] References Cited

U.S. PATENT DOCUMENTS 4,956,416 9/1990 Sanchez .................... 548/210

Primary Examiner—Mary C. Lee
Assistant Examiner—MarySusan H. Gabilan
Attorney, Agent, or Firm—Connolly & Hutz

[57] ABSTRACT

Sulfimidoperoxycarboxylic acids of the formula

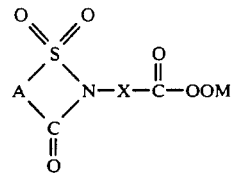

in which
A is a group of the formula

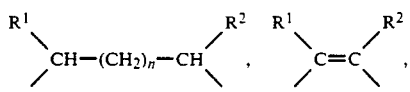

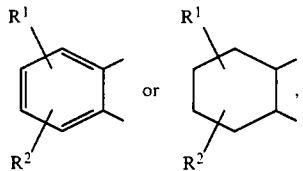

n is the number 0, 1 or 2,
$R^1$ is hydrogen, fluorine, chlorine, bromine, $C_1$-$C_{20}$-alkyl, $C_2$-$C_{20}$-alkenyl, aryl or $C_1$-$C_{10}$-alkylaryl,
$R^2$ is hydrogen, fluorine, chlorine, bromine or a group of the formula $SO_3M$, $CO_2M$ or $OSO_3M$,
M is hydrogen, an alkali metal or ammonium ion or the stoichiometric amount of an alkaline earth metal ion and
X is $C_1$-$C_{19}$-alkylene or ortho-, meta- or para-arylene.

These sulfimidoperoxycarboxylic acids are suitable as bleaches, oxidants or disinfectants.

7 Claims, No Drawings

SULFIMIDOPEROXYCARBOXYLIC ACIDS

The invention relates to sulfimidoperoxycarboxylic acids, a process for their preparation and their use. Inorganic persalts have been known as bleaching additives in detergents for a long time. However, since they only display their optimum bleaching power at temperatures above 60° C., a number of organic compounds are described for activation thereof, which react during the washing process with hydrogen peroxide while releasing a peroxycarboxylic acid which already has a bleaching effect at 40° to 60° C. A survey of numerous known perborate activators such as N-acyl compounds (tetraacetylethylenediamine, tetraacetylmethylenediamine, tetraacetylglycoluril) or activated esters (pentaacetylglucose, sodium acetoxybenzenesulfonate, sodium benzoyloxybenzenesulfonate) is given, for example, in U.S. Pat. No. 4,248,928.

In addition, a number of organic peroxycarboxylic acids have recently been described as bleaching systems for detergents. Besides already commercially available peroxycarboxylic acids such as dodecanediperoxycarboxylic acid (EP-A-127,782) and monoperoxyphthalic acid (EP-A-27,693), persuccinic acid (DE-A-3,438,529), perglutaric acid (DE-A-3,539,036) and sulfoperbenzoic acid have been described. The problem with these peroxycarboxylic acids, however, is their low stability on storage, which is only partly guaranteed by special physical or chemical stabilization. The preparation of magnesium salts (EP-A-105,689) or an addition of phosphane oxide/sodium sulfate (DE-A-3,320,497) has proved particularly suitable here. According to EP-A-170,386, organic peroxycarboxylic acids can also be stabilized by an additional amide group, and according to EP-A-349,940 also by an additional imide group in the molecule.

Moreover, numerous other peroxycarboxylic acids which have stabilizing functional groups have been described, thus, for example, ammoniumperoxycarboxylic acids (EP-A-316,809) pyridine-N-oxideperoxycarboxylic acids (EP-A-300,461) or sulfoneperoxycarboxylic acids (EP-A-267,175).

The present invention relates to sulfimidoperoxycarboxylic acids of the formula

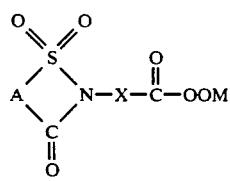

in which A is a group of the formula

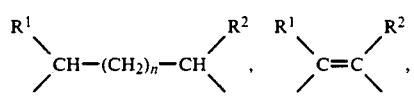

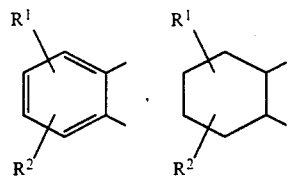

n is the number 0, 1 or 2, $R^1$ is hydrogen, fluorine, chlorine, bromine, $C_1$-$C_{20}$-alkyl, $C_2$-$C_{20}$-alkenyl, aryl, preferably phenyl, or $C_1$-$C_{10}$-alkylaryl, preferably $C_1$-$C_4$-alkylphenyl, $R^2$ is hydrogen, fluorine, chlorine, bromine or a group of the formula $SO_3M$, $CO_2M$ or $OSO_3M$, M is hydrogen, an alkali metal or ammonium ion or the stoichiometric amount of an alkaline earth metal ion and X is $C_1$-$C_{19}$-alkylene or ortho-, meta- or para-arylene, preferably para-phenylene.

Saccharinpercarboxylic acids differing in their alkylene chain, such as, for example, 4-[1,1,3-trioxo-3H-$\lambda^6$-benz[d]isothiazol-2-yl]perbutanoic acid, 6-[1,1,3-trioxo-3H-$\lambda^6$-benz[d]isothiazol-2-yl]perhexanoic acid and 7-[1,1,3-trioxo-3H-$\lambda^6$-benz[d]isothiazol-2-yl]perheptanoic acid, are particularly suitable for the purpose according to the invention.

The saccharinpercarboxylic acids are prepared by the steps
-a- esterification of the bromocarboxylic acid
-b- synthesis of the saccharincarboxylic acid ester
-c- oxidation to the saccharinpercarboxylic acid
-d- isolation of the saccharinpercarboxylic acid The individual steps are illustrated in greater detail in the following. The preparation of the bromocarboxylic acid ester Br-X-COOR³, in which R³ is $C_1$-$C_5$-alkyl, is carried out by acid-catalyzed esterification of the bromocarboxylic acid (Houben-Weyl, Methoden der Organischen Chemie (Methods of Organic Chemistry), E5, p. 65).

Bromocarboxylic acids which can be employed are in particular bromoacetic acid, 3-bromopropionic acid, 4-bromobutyric acid, 6-bromocaproic acid and 7-bromoheptanoic acid.

The saccharincarboxylic acid ester is obtained by reaction of saccharin sodium salt (U.S. Pat. No. 1,601,505, U.S. Pat. No. 2,667,503) with the bromocarboxylic acid ester Br-X-COOR³ in dimethylformamide (J. Org. Chem. 21 (1956), 583) or from 2-sulfobenzoic anhydride and an amino acid ester of the formula H₂N-X-COOR³ (U.S. Pat. No. 2,462,835).

The conversion of the sulfimidocarboxylic acid ester obtained in step -b- to sulfimidopercarboxylic acids is carried out by reaction with an oxidation mixture of hydrogen peroxide and a strong acid. Hydrogen peroxide is usually used as a 30 to 95% strength by weight, preferably 50 to 85% strength by weight, aqueous solution.

Suitable acidic catalysts are sulfuric acid, methanesulfonic acid or an acidic ion exchanger. Sulfuric acid is used as a 50 to 96% strength by weight, preferably 75 to 96% strength by weight, aqueous solution.

Hydrogen peroxide is employed in a molar ratio of 10 to 1:1, preferably 4 to 2:1 per oxidizable carboxyl group of the sulfimidocarboxylic acid ester. The type and amount of the catalyst acid are dependent on the sulfimidocarboxylic acid ester employed. In general, a 1.5 to 6-fold amount by weight—relative to the sulfimidocarboxylic acid ester—is added to the catalyst acid. The reaction temperature depends on the stability of the corresponding sulfimidopercarboxylic acid and is usually between 5° and 60° C., preferably 30° to 45° C.

The claimed sulfimidoperoxycarboxylic acids in general precipitates on addition of water and can be isolated in a simple manner by filtration or centrifugation. It is also possible to precipitate sulfimidoperoxycarboxylic acids which do not precipitate or only precipitate incompletely on addition of water, by addition of aqueous solutions of basic salts.

The sulfimidoperoxycarboxylic acids according to the invention are solid, nearly odorless, have a low vapor pressure and are of excellent thermal stability. They can be used as bleaches for textiles in pure form, preferably as a spot-removing salt, or in acidic liquid formulations having a pH of less than or equal to 6 or can be used in formulations with detergents, preferably as granules, for bleaching textiles. The sulfimidoperoxycarboxylic acids according to the invention can furthermore be used as sanitary cleaners or as disinfectants for medical equipment. The sulfimidoperoxycarboxylic acids according to the invention are also suitable as oxidants in synthetic chemistry, in particular for the epoxidation of olefins.

The preparation of the sulfimidoperoxycarboxylic acids according to the invention is illustrated by the following examples:

EXAMPLE 1

(a) Methyl 2-[1,1,3-trioxo-3H-$\lambda^6$-benz[d]isothiazol-2-yl]acetate 37.8 g (0.2 mol) of anhydrous saccharin sodium salt are initially introduced in 60 ml of anhydrous dimethylformamide (DMF) and a solution of 30.3 g (0.2 mol) of methyl α-bromoacetate in 40 ml of anhydrous DMF is added. The mixture is then stirred at 100° C. for 5 h and, after cooling, 100 ml of water are added dropwise. The reaction product is extracted three times from the aqueous phase by shaking with 100 ml of chloroform each time, the organic phase is dried over sodium sulfate and the solvents are removed on a rotary evaporator. Yield 46.6 g (97.5%) m.p.: 104°–106° C.

$^1$H-NMR (CDCl$_3$, 100 MHz): δ 3.8 (s, 3H), 4.45 (s, 2H), 7.8–8.15 (m, 4H)

(b) 2-[1,1,3-Trioxo-3H-$\lambda^6$-benz[d]isothiazol-2-yl]peracetic acid 23.9 g (0.1 mol) of methyl 2-[1,1,3-trioxo-3H-$\lambda^6$-benz[d]isothiazol-2-yl]acetate are dissolved in 50 g of sulfuric acid (96% strength by weight) and the solution is cooled to 40° C. 10 g (0.25 mol) of hydrogen peroxide (85% strength by weight) are then added dropwise with ice-cooling in such a way that the internal temperature can be kept between 35° and 40° C. 100 ml of water are then added dropwise with cooling, the reaction mixture is extracted five times by shaking with 150 ml of methylene chloride each time, and the organic phase is washed four times using 200 ml of water each time until neutral and dried over Na$_2$SO.

The solvent is removed on a rotary evaporator at a water bath temperature of at most 40° C. and the product is dried at 40° C. in a water pump vacuum.

Yield: 15.7 g (65%) active oxygen content (AO)=3.5% active substance content (AS)=53.7% m.p.: 100° C. (decomposition) $^1$H-NMR (CDCl$_3$, 100 MHz): δ 4.59 (s, 2H), 7.8–8.15 (m, 4H)

EXAMPLE 2

(a) Methyl 3-[1,1,3-trioxo-3H-$\lambda^6$-benz[d]isothiazol-2-yl]propionate 37.8 g (0.2 mol) of anhydrous saccharin sodium salt in 60 ml of anhydrous DMF and 33.4 g (0.2 mol) of methyl β-bromopropionate are reacted as described in Example 1 and the mixture is worked up.

Yield: 47.4 g (94%) m.p.: 63°–64° C. $^1$H-NMR (CDCl$_3$, 100 MHz): δ 2.88 (t, 2H), 3.74 (s, 3H), 4.1 (t, 2H), 7.8–8.13 (m)

(b) 3-[1,1,3-Trioxo-3H-$\lambda^6$-benz[d]isothiazol-2-yl]perpropionic acid 25.3 g (0.1 mol) of methyl 3-[1,1,3-trioxo-3H-$\lambda^6$-benz[d]isothiazol-2-yl]propionate are dissolved in 50 g of sulfuric acid (96% strength by weight) and the solution is cooled to 35° C. 17 g (0.25 mol) of hydrogen peroxide (50% strength by weight) are added dropwise with ice-cooling in such a way that the internal temperature can be kept between 35°–40° C. After stirring at 40° C. for 1 h, approximately a further 100 ml of water are added with cooling. The precipitated peroxycarboxylic acid is filtered off with suction, washed free of mineral acid with water and dried at 40° C. in a water pump vacuum.

Yield: 15.9 g (62.4%), AO=4.27%, AS=68% m.p.: 101°–102° C. (decomposition) $^1$H-NMR (CDCl$_3$, 100 MHz): δ 2.98 (t, 2H), 4.15 (t, 2H), 7.8–8.13 (m).

EXAMPLE 3

(a) Methyl 4-[1,1,3-trioxo-3H-$\lambda^6$-benz[d]isothiazol-2-yl]butanoate 120 g (0.64 mol) of anhydrous saccharin sodium salt in 200 ml of anhydrous DMF and 115 g (0.64 mol) of methyl γ-bromobutanoate in 115 ml of anhydrous DMF are reacted as in Example 1 and the mixture is worked up.

Yield: 168.4 g (98.5%) m.p.: 91°–92° C. $^1$H-NMR (CDCl$_3$, 100 MHz): δ 2.18 (m, 2H), 2.5 (m, 2H), 3.7 (s, 3H), 3.88 (t, 2H), 7.8–8.13 (m, 4H).

(b) 4-[1,1,3-Trioxo-3H-$\lambda^6$-benz[d]isothiazol-2-yl]perbutanoic acid 26.7 g (0.1 mol) of methyl 4-[1,1,3-trioxo-3H-$\lambda^6$-benz[d]isothiazol-2-yl]butanoate, 50 g of sulfuric acid (96% strength by weight) and 17 g (0.25 mol) of hydrogen peroxide (50% strength by weight) are reacted as in Example 2, and the mixture is stirred at 40° C. for 3 h and worked up as in Example 2.

Yield: 24.6 g (91.6%), AO=4.36%, AS=73.4% m.p.: 47°–51° C.

EXAMPLE 4

(a) Methyl 6-[1,1,3-trioxo-3H-$\lambda^6$-benz[d]isothiazol-2-yl]hexanoate 167.4 g (0.89 mol) of anhydrous saccharin sodium salt in 240 ml of anhydrous DMF and 185 g (0.89 mol) of methyl ε-bromocaproate in 160 ml of anhydrous DMF are reacted as described in Example 1 and the mixture is worked up.

Yield: 267.4 g (97%) m.p.: 82°–84° C.

(b)
6-[1,1,3-Trioxo-3H-$\lambda^6$-benz[d]isothiazol-2-yl]perhexanoic acid 29.5 g (0.1 mol) of methyl 6-[1,1,3-trioxo-3H-$\lambda^6$-benz[d]isothiazol-2-yl]hexanoate, 50 g of sulfuric acid (96% strength by weight) and 17 g (0.25 mol) of hydrogen peroxide (50% strength by weight) are reacted as in Example 2, and the mixture is subsequently stirred at 40° C. for 2 h and worked up.

Yield: 28.7 g (96.6%), AO=4.2%, AS=75.3% m.p.: waxy $^1$H-NMR (CDCl$_3$, 100 MHz): $\delta$ 1.3–2.0 (m, 6H), 2.4 (m, 2H), 3.8 (m, 2H), 7.8–8.1 (m, 4H).

EXAMPLE 5

(a) Methyl 7-[1,1,3-trioxo-3H-$\lambda^6$-benz[d]isothiazol-2-yl]heptanoate 238 g (1.26 mol) of anhydrous saccharin sodium salt in 450 ml of anhydrous DMF and 282 g (1.26 mol) of methyl 7-bromoheptanoate in 280 ml of anhydrous DMF are reacted as described in Example 1 and the mixture is worked up.

Yield 394 g (96%) m.p.: 62°–63° C. $^1$H-NMR (CDCl$_3$, 100 MHz): $\delta$ 1.25–2.0 (bm, 8H), 2.3 (t, 2H), 3.65 (s,3H), 3.75 (t, 2H), 7.75–8.1 (m, 4H).

(b)
7-[1,1,3-Trioxo-3H-$\lambda^6$-benz[d]isothiazol-2-yl]perheptanoic acid 30 g (0.1 mol) of methyl 7-[1,1,3-trioxo-3H-$\lambda^6$-benz[d]-isothiazol-2-yl]heptanoate, 50 g of sulfuric acid (96% strength by weight) and 17 g (0.25 mol) of hydrogen peroxide (50% strength by weight) are reacted as in Example 2, and the mixture is stirred between 40° and 43° C. for 2 h and worked up.

Yield: 28.8 g (92.6%), AO=4.44%, AS=86.4% m.p.: 63°–64° C.

Washing tests in the Launder-o-meter

The washing tests are carried out in a preheated Launder-o-meter at temperatures of 20°, 40° and 60° C. using water of water hardness 15° dH. The washing time is in each case 30 min.

1.5 g/l of phosphate-free WMP detergent (Krefeld laundry research) are added as the test detergent. The peracids in powdered form are added such that on complete dissolution they can in each case liberate 25 mg/l of active oxygen.

Tea on cotton (Krefeld laundry research) and red wine on cotton (EMPA., Switzerland) are used as standard stains. The bleaching power is given as the reflectance after washing, measured at 460 nm.

Tetraacetylethylenediamine (TAED) in combination with perborate monohydrate is employed as the comparison substance.

|  | Reflectances | | |
| --- | --- | --- | --- |
| Compound | 20° C. | 40° C. | 60° C. |
| Tea/cotton | | | |
| according to Example 1 | 62.9 | — | — |
| according to Example 2 | 63.8 | — | — |
| according to Example 3 | 62.1 | 71.8 | 74.6 |
| according to Example 4 | 61.1 | 69.4 | 74.2 |
| TAED/perborate | 58.1 | 66.4 | 72.0 |
| Red wine/cotton | | | |
| according to Example 1 | 65.7 | — | — |
| according to Example 2 | 63.4 | — | — |
| according to Example 3 | 62.2 | 71.6 | 76.9 |
| according to Example 4 | 62.1 | 70.4 | 75.7 |
| TAED/perborate | 57.9 | 65.9 | 68.2 |

The washing tests show that the sulfimidoperoxycarboxylic acids according to the invention have higher reflectances at 20° C., 40° C. and 60° C. and thus a better bleaching power than the comparison substance TAED/perborate.

We claim:

1. A sulfimidoperoxycarboxylic acid of the formula $$\begin{array}{c} O \diagdown \diagup O \\ S \\ \diagup \diagdown \\ A \quad N-X-C-OOM \\ \diagdown \diagup \quad \| \\ C \quad O \\ \| \\ O \end{array}$$

in which
A is a group of the formula $$\begin{array}{cc} R^1 \qquad R^2 & R^1 \qquad R^2 \\ \diagdown \diagup & \diagdown \diagup \\ CH-(CH_2)_n-CH , & C=C , \\ \diagup \diagdown & \diagup \diagdown \end{array}$$

(ortho-disubstituted benzene with R$^1$, R$^2$) or (disubstituted cyclohexane with R$^1$, R$^2$), n is the number 0, 1 or 2,
R$^1$ is hydrogen, fluorine, chlorine, bromine, C$_1$–C$_{20}$-alkyl, C$_2$–C$_{20}$-alkenyl, aryl or C$_1$–C$_{10}$-alkylaryl,
R$^2$ is hydrogen, fluorine, chlorine, bromine or a group of the formula SO$_3$M, CO$_2$M or OSO$_3$M,
M is hydrogen, an alkali metal or ammonium ion or the stoichiometric amount of an alkaline earth metal ion and
X is C$_1$–C$_{19}$-alkylene or ortho-, meta- or para-arylene.

2. A compound as claimed in claim 1, in which A is a group of the formula (disubstituted benzene with R$^1$, R$^2$)

in which
R$^1$ is hydrogen, fluorine, chlorine, bromine, phenyl or C$_1$–C$_4$-alkylphenyl,
R$^2$ is hydrogen, fluorine, chlorine, bromine or a group of the formula SO$_3$M, COOM or OSO$_3$M,
M is hydrogen, an alkali metal or ammonium ion or the stoichiometric amount of an alkaline earth metal ion and
X is C$_1$–C$_{19}$-alkylene or para-phenylene.

3. A compound as claimed in claim 2, in which A, $R^1$, $R^2$ and M have the meaning described there and X is $C_1-C_6$-alkylene.

4. A saccharinperoxycarboxylic acid as claimed in claim 3, in which A, M and X have the meaning described there and $R^1$ and $R^2$ are each hydrogen.

5. A bleach comprising the sulfimidoperoxycarboxylic acid as claimed in claim 1.

6. An oxidant comprising the sulfimidoperoxycarboxylic acid as claimed in claim 1.

7. A disinfectant comprising the sulfimidoperoxycarboxylic acid as claimed in claim 1.

* * * * *